Figure 1A:
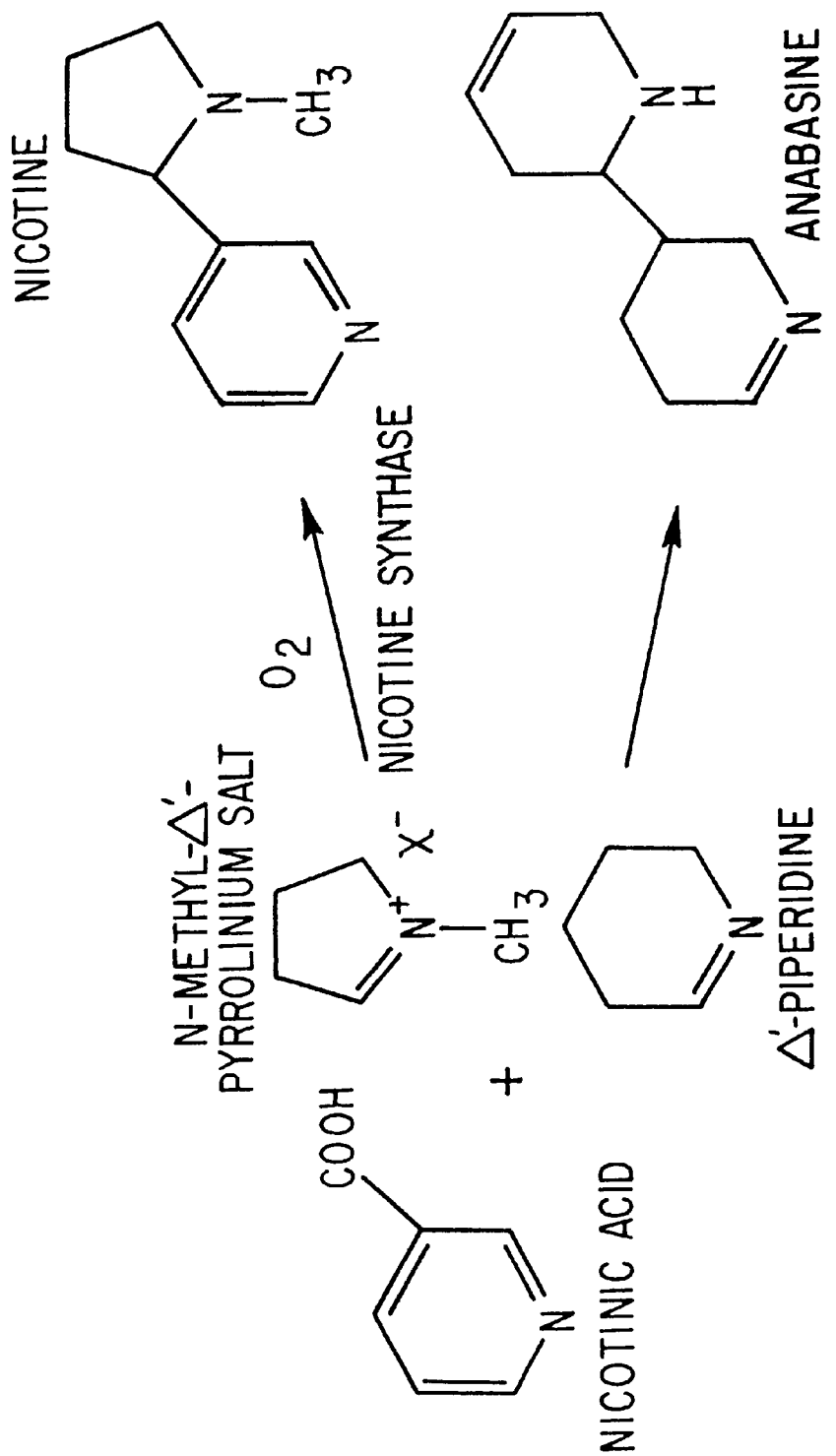

US005959187A

United States Patent [19]
Bailey et al.

[11] Patent Number: 5,959,187
[45] Date of Patent: Sep. 28, 1999

[54] EXPRESSION OF OXYGEN-BINDING PROTEINS IN PLANTS

[76] Inventors: James E. Bailey, Winkelwiese 6, Zurich, Switzerland, CH-8001; Leif Bülow, Borgåslingan 6, Lund, Switzerland, 224 72

[21] Appl. No.: 08/720,260

[22] Filed: Sep. 26, 1996

[51] Int. Cl.⁶ .............................. A01H 5/00; C12N 5/14; C12N 15/31; C12N 15/82
[52] U.S. Cl. ..................... 800/317.3; 435/320.1; 435/419; 435/468; 435/469; 435/470; 536/23.7; 800/278; 800/282; 800/287; 800/298; 800/306; 800/312; 800/317.2; 800/317.4; 800/320.1; 800/320.2; 800/320.3; 800/322; 800/323; 800/323.1
[58] Field of Search .......................... 435/172.3, 320.1, 435/419, 468, 469, 470; 800/205, 278, 282, 287, 298, 306, 312, 317.2, 317.3, 317.4, 320.1, 320.2, 320.3, 322, 323, 323.1; 536/23.7

[56] References Cited

U.S. PATENT DOCUMENTS 5,049,493  9/1991  Khosla et al. ........................ 435/69.1

OTHER PUBLICATIONS

Bailey, J., 1991, "Toward a Science of Metabolic Engineering," *Science* 252:1668–1675.
Berlin, J. et al., 1994, *Stud. Plant Sci.* 4:57–81.
Bogusz et al., 1988, "Functioning haemoglobin genes in non–nodulating plants," *Nature* 331:178–180.
Breuling, M. et l., 1985, *Plnt Cell Rep.* 4:220–223.
Chen, W. et al., 1994, *Biotechnol. Prog.* 10:308–313.
DeModen, J.A. et al., 1993, *Bio/Technology* 11:926–929.
Friesen, J.B. and Leete, E., 1990, *Tetrahedron Lett.* 31:6295–6298.
Kallio et al., 1994, "Intracellular Expression of Vitreoscilla Hemoglobin Alters *Escherichia coli* Energy Metabolism under Oxygen–Limited Conditions," *Eur. J. Biochem.* 219:201–208.
Kallio, P.T. and Bailey, J.E., 1996, "Intracellular Expression of Vitreoscilla Hemoglobin (VHb) Enhances Total Protein Secretion and Improves the Production of α–Amylase and Neutral Protease in *Bacillus subtillis*," *Biotechnol. Prog.* 12:31–39.
Khosia, C. et al., 1990, *Bio/Technology* 8:849–853.
Khosla, C., Bailey, J.E., 1988, *Mol. Gen. Genet.* 214:158–161.
Khosia, C., Bailey, J.E., 1988, *Nature* 331:633–635.
Khosla, C. and Bailey J.E., 1989, *J. Mol. Biol.* 210:79–89.
Knauf, 1995, *Curr. Opin. Biotech.* 6:165–70.
Lilius, G., Holmberg, N. and Bülow, L., 1996, *Bio/Technology* 14:177–180.
Magnolo, S.K. et al., 1991, *Bio/Technology* 9:473–476.
Pendse, G.J. and Bailey, J.E., 1994, *Biotechnol. Bioeng.* 44:1367–1370.
Robins, R.J. et al., 1991, *Planta Med.* 57:27–35.

Robson et al., 1996, "Genetic engineering of harvest index in tobacco through overexpression of a phytochrome gene," *Nature Biotechnology* 14:995–998.
Saiki, et al., 1988, *Science* 239:487–491.
Sander, F. et al., 1994, *Proc. 6th Eur. Congress Biotechnol.*, Alberghina, L., Frontali, L. and Sensi, P. (eds.) Elsevier Science B.V., Amsterdam 607–610.
Schaltmann, J.E. et al., 1995, *Biotech. Bioeng.* 45:435–439.
Tsai et al., 1995, "Improvement of *Escherichia coli* Microaerobic Osygen Metabolism by Vitreoscilla Hemoglobin: New Insights from NAD(P)H Fluorescence and Culture Redox Potential," *Biotechnol. Bioeng.* 47:347–354.
Tsai et al., 1996, "Effect of Vitreoscilla Hemoglobin Dosage on Microaerobic *Escherichia coli* Carbon and Energy Metabolism," *Biotechnol. Bioeng.* 49:139–150.
Tsai et al., 1996, "Intracellular Expression of Vitreoscilla Hemglobin Modifies Microaerobic *Escherichia coli* Metabolism Through Elevated Concentration and Specific Activity of Cytochrome o," *Biotechnol. Bioeng.* 49:151–160.
Zhu et al., 1992, "Yeast flavohemoglobin is an ancient protein related to globins and a reductase family," *Proc. Natl. Acad. Sci. U.S.A.* 89:5015–5019.
Stam M, et al. "The silence of genes in transgenic plants." Ann. Bot. 79:3–12, 1997.
Koziel MG, et al. "Optimizing expression of transgenes with an emphasis on post–transcriptional events." Plant Mol. Biol. 32:393–405, 1996.
Smith CJS, et al. "Antisense RNA inhibition of polygalacturonase gene expression in transgenic tomatoes." Nature 334:724–726, Aug. 25, 1988.
Rothstein SJ, et al. "Promoter cassetees, antibiotic–resistance genes, and vectors for plant transformation." Gene 53:153–161, 1987.
Landsmann J, et al. "Organ regulated expression of the Parasponia–andersonii hemoglobin gene in transgenic tobacco plants." Mol. Gen. Genet. 214:68–73, 1988.

*Primary Examiner*—Lynette F. Smith
*Assistant Examiner*—Amy J. Nelson
*Attorney, Agent, or Firm*—Pennie & Edmonds LLP

[57] ABSTRACT

The present invention relates to genetic-engineering of plants for enhanced oxygen assimilation and utilization. More particularly, this invention relates to producing transgenic plants engineered to express oxygen-binding proteins such as, for example, hemoglobin, myoglobin, and hemoproteins. The engineered plants of the invention achieve quicker germination, are faster growing or maturing crops, produce higher crop yields, and/or contain higher levels of desired plant metabolites, particularly alkaloids.

38 Claims, 5 Drawing Sheets

EXPRESSION OF OXYGEN-BINDING PROTEINS IN PLANTS

1. INTRODUCTION

The present invention relates to genetic-engineering of plants for enhanced oxygen assimilation and utilization. More particularly, this invention relates to producing transgenic plants engineered to express oxygen-binding proteins such as, for example, hemoglobin, myoglobin, and hemoproteins. The engineered plants may be used to achieve quicker germination, faster growing or maturing crops, higher crop yields and/or plants with higher levels of desired plant metabolites, particularly alkaloids.

2. BACKGROUND OF THE INVENTION

Genetic engineering of plants through transgenic approaches has rapidly become a diverse and promising field. Transformation techniques are applied both to study plant development and physiology, and in attempts to generate plants with advantageous agricultural properties.

For example, much effort has focused on improving crop production by transforming plants with herbicide or pesticide resistance genes. When grown under field conditions, the resulting transgenic plants can tolerate and survive applications of herbicides or pesticides which would destroy non-transformed plants. Alternatively, plants themselves have been genetically engineered to express products which are shown to act as natural insecticides such as *Bacillus thuringensis* toxin proteins (see U.S. Pat. No. 5,380,831, issued Jan. 10, 1995).

Genetic engineering has also been attempted to generate plants with altered compositions of primary metabolites such as starch, sugar, and oils. For example, a bacterial levan sucrase gene was transformed into plants to increase levels of fructans in the resulting transformant. In another approach, the activity of certain enzymes involved in the metabolic synthesis of oils has been decreased using anti-sense technology in order to design vegetable oils exhibiting the desired properties. (Reviewed in Knauf, 1995, *Curr. Opin. Biotech.* 6: 165–70).

In addition to attempts to alter primary metabolic compositions of plants (i.e. carbohydrates, oils, amino acids and proteins), it would also be desirable to alter secondary metabolite compositions. Secondary metabolites are those specialized plant products required by cells in small amounts (e.g. hormones), or are highly specialized biomolecules (e.g. nucleotides, pigments, toxins, antibiotics, and alkaloids). Generally, secondary metabolites can be defined as compounds that have no recognized role in the maintenance of fundamental life processes of the cell, but which may perform other advantageous functions for the organism as a whole. (See for example, Bell, 1981, "The Physiological Role(s) of Secondary (Natural) Products" in *The Biochemistry of Plants*, v. 7, p. 1, Academic Press, Inc.)

The production of useful secondary metabolites from plants and plant cell cultures is an important aspect of plant technology. About 25% of the prescription drugs used in the industrialized world contain ingredients extracted from higher plants (Tyler, V. E., 1988, *Planta Med.* 54: 95–100). The most prominent group of plant substances used in medicine are the alkaloids (Nickell, L. G., 1980, "Products," *Plant tissue culture as a source of biochemicals*, Staba, E. J., Ed., Boca Raton, CRC Press Inc., 235–269). Alkaloids are secondary metabolites which protect plants against phytophagocytosis by higher organisms or invasion by pathogens (Robins, R. J. et al., 1991, *Planta Med.* 57: 27–35). Plant alkaloids are generally derived from simple amino acids that interact with acetate and terpenoid units and undergo aromatic hydroxylations (Robins, supra). Examples of plant alkaloids are nicotine, scopolamine, hyoscyamine, ajmalicine, serpentine, piperine, leucenol, mimosine, ricinine, pelletierine, cocaine, hygrine, lupinine and anagyrine.

Several examples of introducing a new metabolic pathway or redirecting previously existing ones to increase production of secondary metabolites have been described (Bailey, supra; Berlin, J. et al., 1994, *Stud. Plant Sci.* 4: 57–81; Lilius, G., Holmberg, N. and Bülow, L., 1996, *Bio/Technology* 14: 177–180). However, apparently all of these genetic engineering approaches entail either the up-regulation of a limiting enzyme in the pathway (through transformation and expression of the cloned gene), or the down-regulation of competing enzymatic pathways (through anti-sense technology). (See for review, Robins et al., 1991, *Planta. Med.* 57: 27–35.)

Plant cell suspension cultures have often been used for industrial production of plant secondary metabolites. During in vitro culture, a critical parameter influencing secondary metabolite formation, especially in scale-up cultures, is the level of dissolved oxygen. For instance, it has been demonstrated that a high dissolved oxygen concentration promotes the production of ajmalicine in Catharantus roseus batch cultures (Schaltmann, J. E. et al., 1995, *Biotech. Bioeng.* 45: 435–439). Similarly, increased alkaloid levels with increasing aeration have been observed in *Berberis wilsonae* (Breuling, M. et al., 1985, *Plant Cell Rep.* 4: 220–223). From these results it has been suggested that oxygen is a limiting substrate in plant tissue culture secondary metabolism, as well as for primary metabolism, especially for industrial scale-up processes. However, this need for increased oxygen has always been thought to be a need for extracellular oxygen during fermentation batch processes.

Aerobic metabolism has been successfully enhanced in fermentation microorganisms and cultured mammalian cells by engineering the host to express the Vitreoscilla hemoglobin gene (VHb) (Khosla, C., Bailey, J. E., 1988, *Nature* 331: 633–635; Khosla, C., Bailey, J. E., 1988, *Mol. Gen. Genet.* 214: 158–161; DeModena, supra; Chen, W. et al., 1994, *Biotechnol. Prog.* 10: 308–313; Pendse, G. J. and Bailey, J. E., 1994, *Biotechnol. Bioeng.* 44: 1367–1370). This metabolic engineering strategy has been shown effective, for example, in increasing total cell protein synthesis by oxygen-limited *Escherichia coli* (Khosla, C. et al., 1990, *Bio/Technology* 8: 849–853 and U.S. Pat. No. 5,049, 493, issued Sep. 17, 1991), improving lysine yield and titer in cultivations of *Corynebacterium glutamicum* (Sander, F. et al., 1994, *Proc. 6th Eur. Congress Biotechnol.,* Alberghina, L., Frontali, L. and Sensi, P. (eds.) Elsevier Science B. V., Amsterdam 607–610), and in increasing actinorhodin and cephalosporin C production in *Streptomyces coelicolor* and *Acremonium chrysogenum*, respectively (Magnolo, S. K. et al., 1991, *Bio/Technology* 9: 473–476; DeModena, J. A. et al., 1993, *Bio/Technology* 11: 926–929).

Hemoglobin and globin-like proteins exist ubiquitously in mammals, and are less frequently found in plants. The few plant hemoglobin-like molecules described, which include lupin and soybean leghemoglobin, are largely thought to be associated with nitrogen-fixation activities of these plants, although some researchers claim that hemoglobin-like proteins occur in the roots of all plants. However, in no case have these proteins been overexpressed in plants. Although several major plant metabolic pathways are known to be oxygen-dependent, including chlorophyll and heme biosynthesis, fatty acid desaturation and cysteine, glycine and serine biosynthesis, oxygen has not been thought to be a limiting factor in metabolism in intact plants. Rather, the observed effects of dissolved oxygen on metabolism in plant tissue cultures has been attributed to mass transport problems during large-scale, or even batch culture, fermentations (see Schlatmann et al., 1991, supra.). Thus, until the present invention, the advantages of altering useable levels of intracellular oxygen in intact plants have not been recognized.

3. SUMMARY OF THE INVENTION

The present invention is directed to the generation of plants with improved agronomic or medicinal characteristics by metabolically engineering an increased intracellular oxygen level or increased utilization of oxygen. Such engineered plants display enhanced production of valuable secondary metabolites, in particular those metabolites which are synthesized by oxygen-dependent pathways, as well as other unexpected and valuable properties such as more rapid germination, higher levels of chlorophyll, increased overall growth metabolism, and increased rate of accumulation of biomass.

The invention encompasses both genetically engineered plants and methods of producing the same. Therefore, in one of its embodiments, the invention encompasses a method of metabolically engineering plants by increasing intracellular levels of oxygen or intracellular utilization of oxygen. The invention includes a method of producing a plant with an improved agronomic or medicinal characteristic by transforming the plant with polynucleotides encoding an oxygen-binding protein. Particularly preferred oxygen-binding proteins are globins, which reversibly bind oxygen through a heme group. In an exemplary embodiment, the oxygen-binding protein is Vitreoscilla hemoglobin. Preferably, the polynucleotides encoding the oxygen-binding protein are operably linked to a strong, constitutively expressed plant promoter, for example, the CaMV 35S promoter.

Another aspect of the invention is a plant or plant cell which has been genetically engineered by the methods of the invention. The invention encompasses plants and plant cells which are both dicotyledons and monocotyledons. Mutants of VHb which bind oxygen are also within the scope of the present invention, as well as methods of obtaining and screening for such mutants, and nucleotide sequences which encode such mutants.

4. BRIEF DESCRIPTION OF THE FIGURES

Figure 1B:
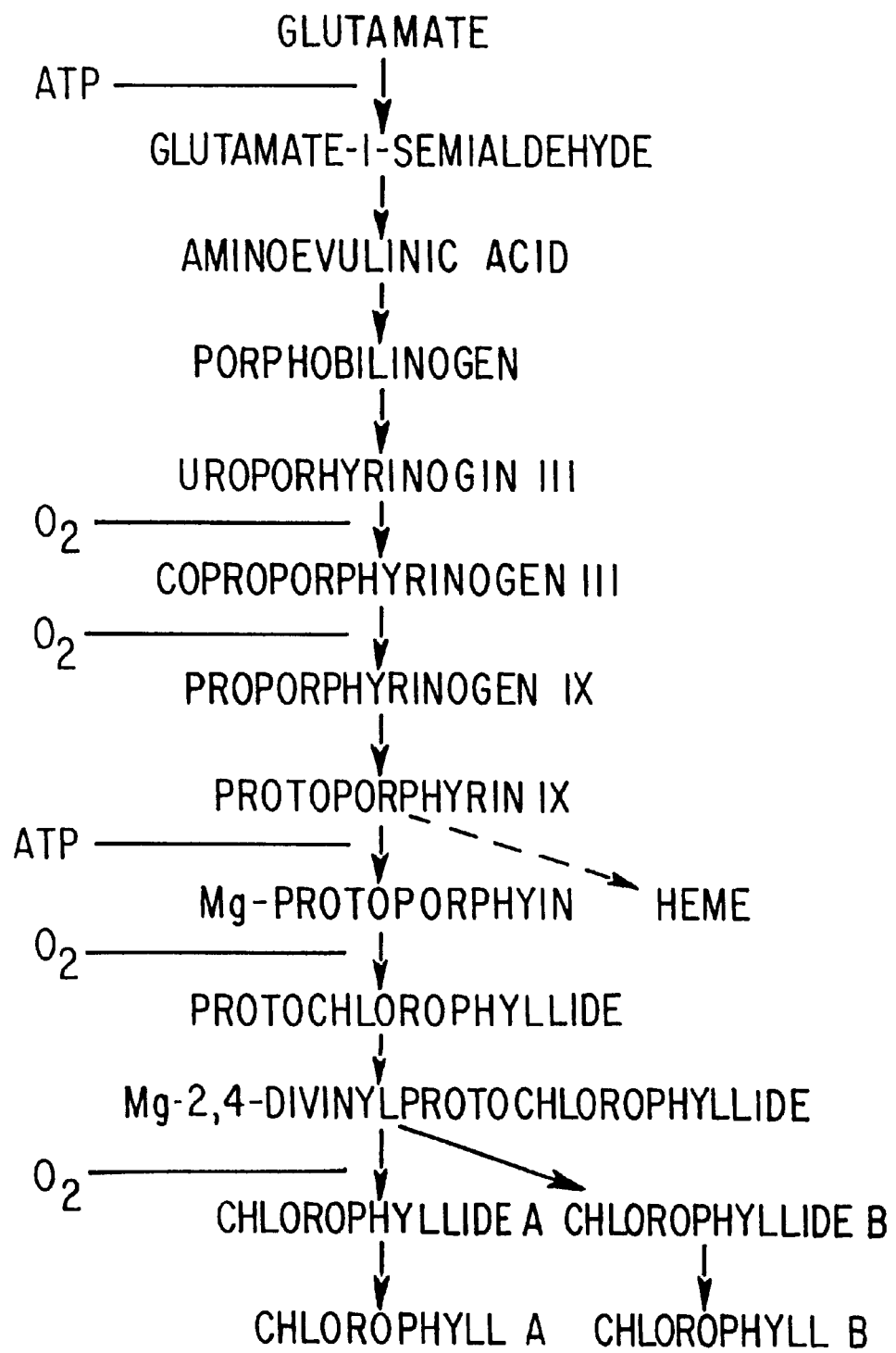

FIGS. 1A–1B: FIG. 1A. The last steps in the *Nicotiana tabaccum* biosynthesis of the secondary metabolites nicotine and anabasine. The reaction catalyzed by nicotine synthase, the oxygen-dependent enzyme catalyzing the conversion of nicotinic acid and N-methyl-Δ'-pyrrolinium salt into nicotine, is labelled in bold. FIG. 1B. Oxygen-dependent steps in chlorophyll and heme biosynthesis in plants. The last oxidation of chlorophyll a to chlorophyll b has only been observed in vitro (Scheer, H. (ed.), 1991, *Chlorophylls* CRC Press, Boca Raton, Fla., USA 421–425).

Figure 2:
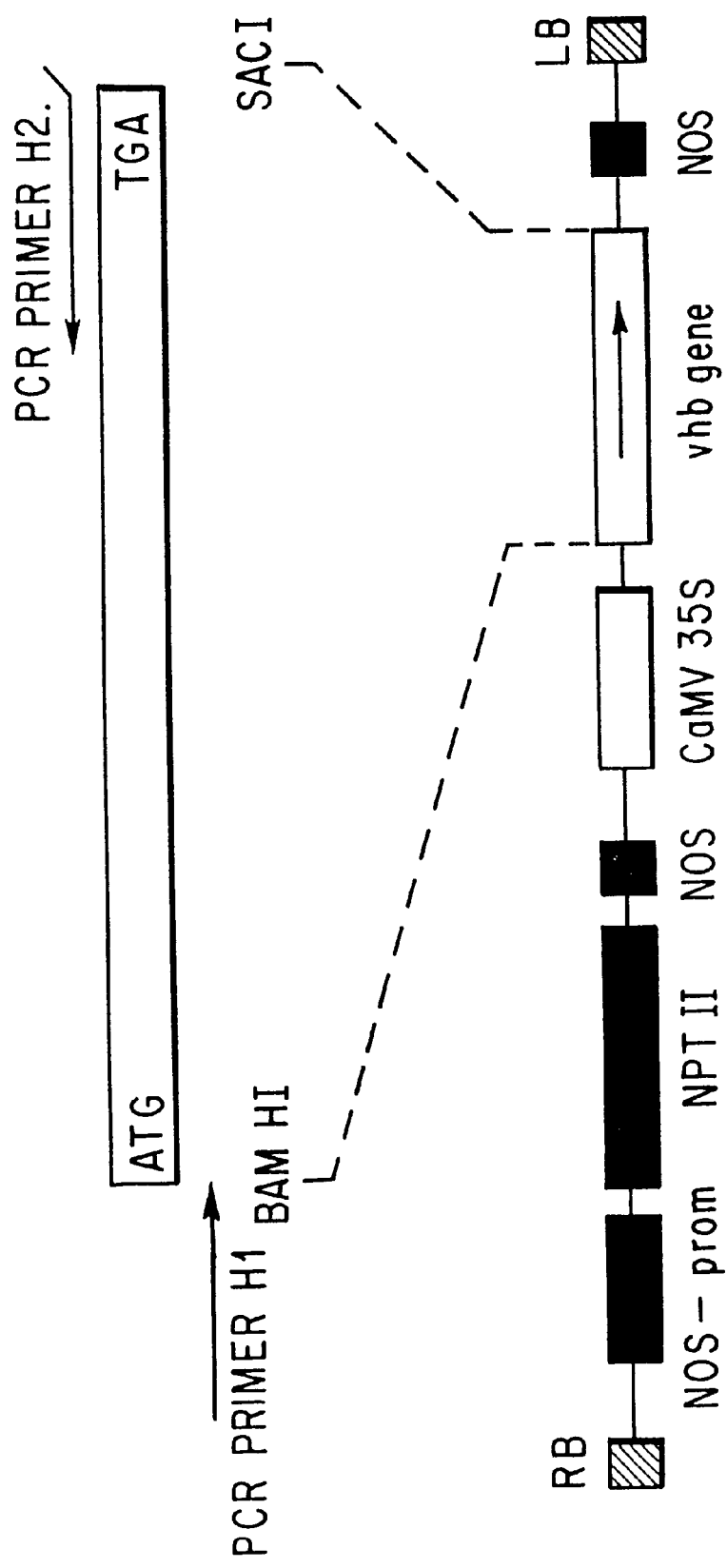

FIG. 2. Construction of the Ti-expression vector containing the Vitreoscilla VHb gene using PCR. The gene was placed under control of the CaMV 35S promoter and transcription termination was achieved by the NOS region. The approximate positions of the PCR primers are indicated by solid arrows. Right and left border of the T-DNA are indicated by RB and LB, respectively. NOS-prom, NPT II and NOS are abbreviations for the nopaline synthase promoter, the neomycine phosphotransferase II gene, and the nopaline synthase 3' transcription termination region, respectively.

Figure 3:
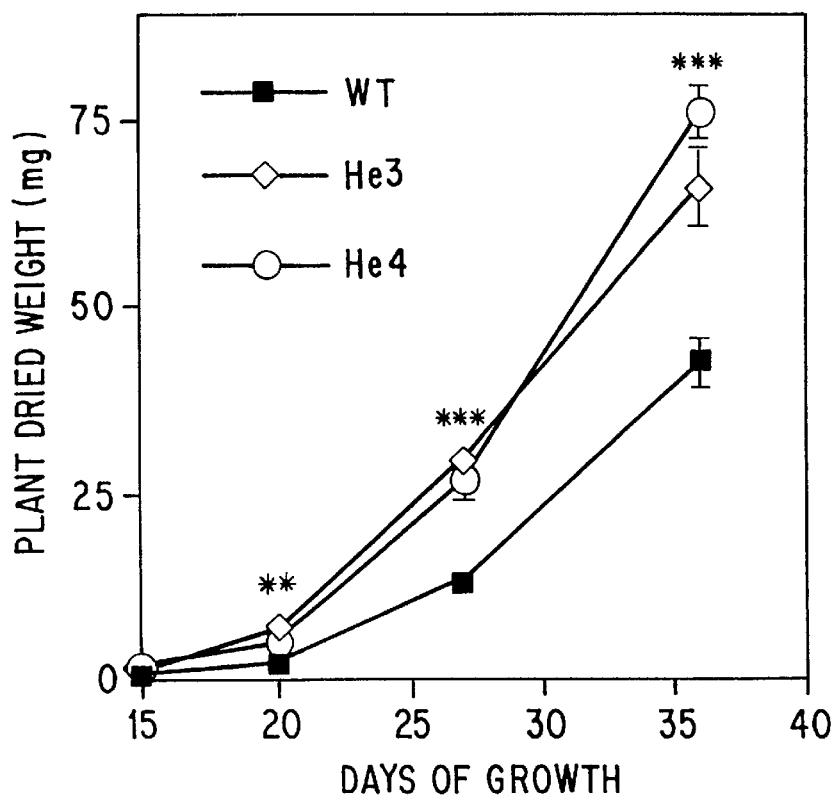

FIG. 3. Dried weight measurements at different time intervals are shown as mean values. Bars correspond to the standard error. The data from the first two time points (15 and 20 days) correspond to 12 plants but weighed in triplets, and the data from the last two time points are from 8 plants individually weighed. This experiment was duplicated and the data points were subjected to statistical analysis using one-way analysis of variance (ANOVA).

Figure 4:
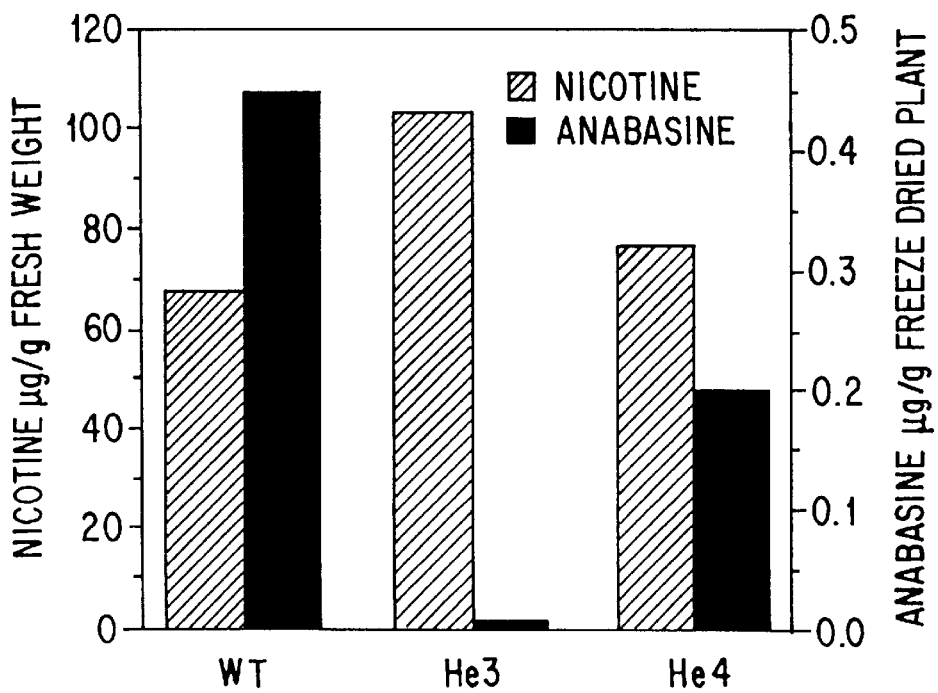

FIG. 4. Nicotine and anabasine production in the transgenic lines, He3 and He4, and a wild-type line. The nicotine concentrations are given μg/g fresh weight and the anabasine concentrations as μg/g freeze-dried plant. The nicotine and anabasine concentrations were measured in eight plants and six plants, respectively. All measurements were performed in duplicate, with the standard deviations being less than 1% and 25%, respectively.

Figure 5:
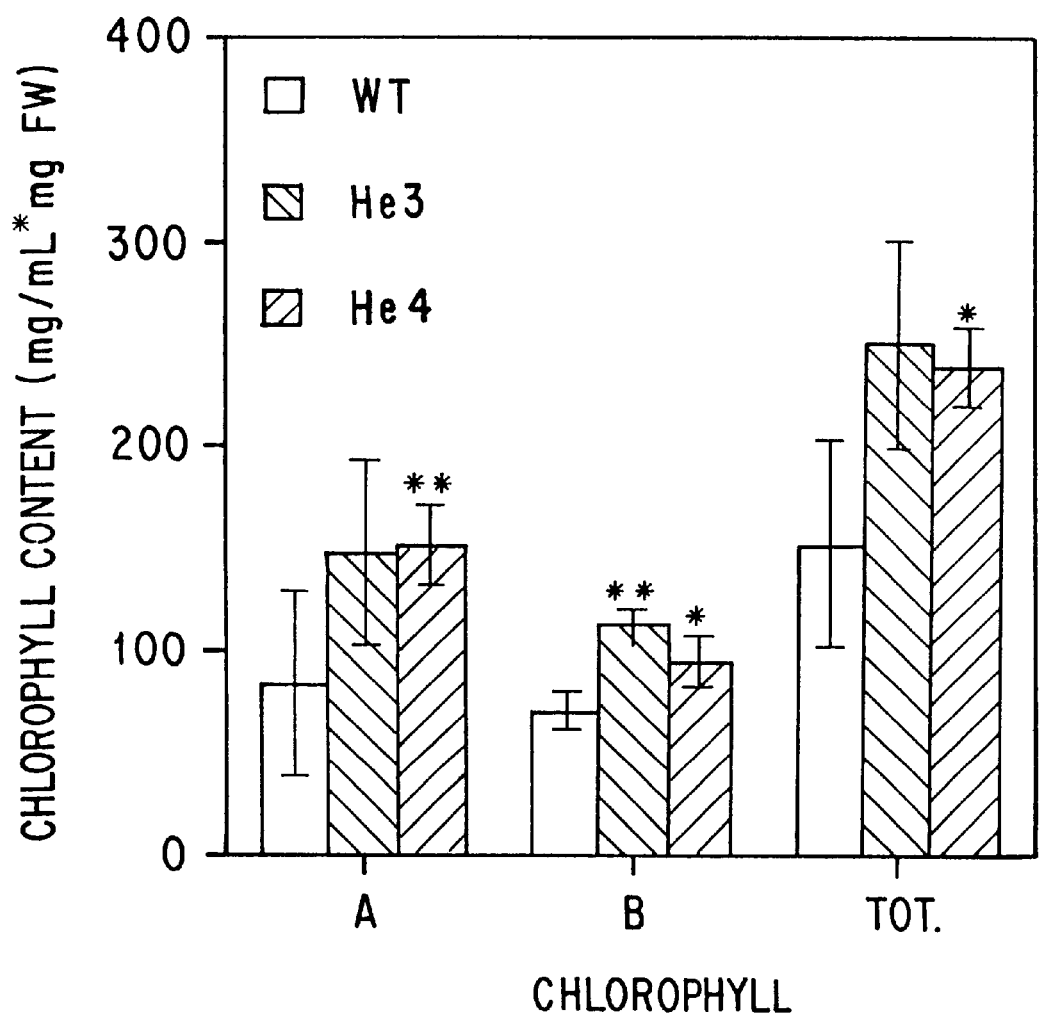

FIG. 5. The chlorophyll contents in the two transgenic tobacco lines and a wild-type control measured as μg chlorophyll/ml×mg fresh weight. The bars represent the mean values of 18 plants. The standard errors of the mean were less than 10%, 8% and 5% for wild-type tobacco, He3 and He4, respectively.

5. DETAILED DESCRIPTION OF THE INVENTION

The present invention relates to metabolic genetic engineering by effectively increasing the intracellular level of available oxygen in plants. The invention is based, in part, on the discovery that transforming plants so as to express oxygen-binding proteins, and in particular heme-containing globins, improves the properties of the transformed plants in unexpected ways. The resulting plants produce higher levels of secondary metabolites whose production is oxygen sensitive surprisingly, however, these genetically engineered plants also exhibit better growth characteristics, more rapid germination, and improved vegetative yield. Without intending to be limited to a particular mechanism, it is believed that these surprising results are due to either an increased level of intracellular oxygen, or an increased efficiency in intracellular oxygen utilization.

Accordingly, the targets for engineering are genes encoding proteins involved in binding oxygen, particularly those which bind oxygen reversibly such as the globins. The target genes include, but are not limited to, those encoding Vitreoscilla hemoglobin (VHb), horse heart myoglobin, *E. coli* hemoprotein, *B. subtilis* hemoprotein, yeast flavohemoglobin, soybean leghemoglobin, lupin leghemoglobin, and sperm whale myoglobin.

Particularly suitable for use in the present invention are those oxygen-binding proteins which have relatively high $k_{off}$ rates such as VHb ($k_{off}$ 5600 s$^{-1}$; Orii and Webster, 1986, *J. Biol. Chem.* 261: 3544–3547) or relatively low oxygen affinity such as horse heart myoglobin ($K_D$ 0.79 μM; Wittenberg et al., 1985, in *Nitrogen fixation research progress*, H. J. Evand et al. Eds. Martinus Nijhoff Publishers, Dordrecht, p. 354). Therefore, particularly preferred oxygen binding proteins may be those proteins with a $k_{off}$ rate for oxygen of greater than 10 s$^{-1}$, or a $K_D$ more than 0.5 μM, although it will be understood that oxygen-binding proteins with rate constants outside of these parameters will also be useful. Other examples of preferred oxygen-binding proteins are globins such as hemoglobin, myoglobin, and leghemoglobins. The properties of many oxygen-binding proteins, including globins, are disclosed in the literature. Additionally, techniques for determining the oxygen-binding properties of a protein such as a globin are well known to one of skill in the art and may be performed without undue experimentation.

A particularly advantageous oxygen-binding protein for use in the instant invention, as described herein by way of working example, is Vitreoscilla hemoglobin ("VHb"). The complete sequence of the VHb gene is described in U.S. Pat. No. 5,049,493, supra. Mutants of VHb which bind oxygen are also within the scope of the present invention. As described more fully below by way of a working example, genes encoding functional mutants of VHb are generated through PCR mutagenesis, and then tested in a simple phenotypic screen for their ability to bind oxygen. Using these technique, several VHb mutants have been obtained for use in the present invention.

Also encompassed within the scope of the invention are any nucleotide sequence which hybridizes to the complement of the nucleotide sequence of the VHb gene under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and any nucleotide sequence that hybridizes to the complement of the nucleotide sequence of the VHb gene under less stringent conditions, such as moderately stringent conditions, e.g., washing in 0.2×SSC/0.1% SDS at 42° C. (Ausubel et al., 1989, supra), yet which still encodes a functionally equivalent Vhb gene product. Functional equivalents of VHb include naturally occurring hemoglobin genes present in other species, and mutant VHb whether naturally occurring or engineered which retain at least some of the functional activity of VHb (i.e., reversible oxygen binding). Species from which genes encoding functional equivalents of VHb include but are not limited to bacterial species, and in particular those bacterial species found in soil, dung, and in other oxygen-accessible, but poorly aerated, environments.

Furthermore, using the teachings of the present invention one of skill in the art can also isolate genes encoding other bacterial proteins which reversibly bind oxygen through a heme group without relying upon sequence homology with known proteins. For example, one may isolate and culture a bacterial organism, prepare genomic DNA from the cultured bacteria, and then construct an expression library with the DNA in *E. coli* using well known techniques. The expression library is plated to obtain isolated colonies. Those *E. coli* colonies carrying plasmids which expresses an oxygen-binding heme protein may be identified phenotypically by their red color. The expression library DNA clones encoding oxygen-binding proteins may be further characterized and subcloned into plant expression vectors. The expression of such oxygen-binding heme proteins in plants is accordingly encompassed by the invention.

The invention also encompasses degenerate variants of nucleotide sequences which encode the amino acid sequence of the VHb protein, VHb mutants, and functional equivalents of VHb encoded by nucleotide sequences which hybridize to the complement of the nucleotide sequence of the VHb gene. For example, the nucleotide sequence may be altered so as to optimize amino acid codon usage for expression in the chosen host cell.

The levels of oxygen-binding proteins can be altered or their expression can be enhanced or otherwise modified (e.g., ectopic expression or tissue specific expression) to engineer a plant with desirable properties. The engineering is accomplished by transforming plants with nucleic acid constructs described herein. The transformed plants or their progenies are screened for plants that express the desired protein or exhibit the desired altered expression of the oxygen-binding protein, altered expression of the corresponding mRNA, altered secondary metabolite levels, increased growth rate, enhanced vegetative yield and/or increased germination rate.

Engineered plants exhibiting the desired physiological and/or agronomic changes can be used in plant breeding or directly in agricultural production. These plants having one altered protein also may be crossed with other altered plants engineered with alterations in other pathways (e.g., cross a oxygen-binding expressing plant to a plant which has been otherwise genetically engineered) to produce lines with even further enhanced physiological and/or agronomic properties compared to the parents.

The invention is illustrated by working examples of plants engineered for expression of Vitreoscilla hemoglobin (VHb). In all instances, engineered plants that exhibit expression also show better growth characteristics, increased rate of seed germination, improved vegetative yield and/or enhanced levels of secondary metabolites over control, wild-type plants.

The invention is based, in part, on the surprising discovery that transformation of plants with oxygen-binding proteins provides several advantages. Plants were transformed with expression plasmids encoding an oxygen-binding protein was an attempt to develop plants with increased drought tolerance. As a model system, Nicotiana tabaccum (tobacco) was first chosen to be transformed with expression constructs encoding the oxygen-binding protein Vitreoscilla hemoglobin (VHb). However, since there is an oxygen-dependent step in the nicotine biosynthesis pathway, the production of nicotine was examined.

The VHb gene was introduced into Nicotiana tabaccum (tobacco) via Agrobacterium mediated gene transfer. Transcription and translation of the VHb gene and message were demonstrated by reverse transcriptase PCR and Western immunoblot analysis, respectively. Transgenic tobacco plants expressing VHb exhibited on average 34% greater nicotine content than wild-type controls. They also contained an altered distribution of nicotine relative to the less desirable alkaloid anabasine. Additional effects of VHb expression on the physiology of the transgenic tobacco plants were also noted; these plants contained on average 10–20% more chlorophyll than controls. Moreover, the plants germinated more quickly and exhibited a more rapid rate of dry weight increase. Thus, engineering of plants to express additional oxygen-binding proteins not only produced increased alkaloid levels and altered distributions of alkaloids, but also enhanced plant growth.

In yet another illustration of the advantages of the present invention, plants from the genus Datura were transformed with the same expression construct used to transform the tobacco plants. Datura is the major commercial source for production of the secondary metabolites scopolamine and hyoscyamine, which are used as sedatives and as starting material for semisynthetic derivatives of these metabolites. Surprisingly, scopolamine and hyoscyamine levels in the transgenic plants were increased as much as 5 to 6 fold over levels found in non-transformed plants.

Thus, the present invention is generally applicable for altering the oxygen utilization in order to obtain plant varieties with advantageous medicinal and agronomic qualities. For example, plants which germinate more quickly and accumulate biomass more rapidly will find particular application in agricultural environments where arable land and/or the length of growing season are limiting factors to production. Even a small increase in biomass production and/or rate of growth can prove significant. Additionally, the increased levels of economically important secondary metabolites may enable production of metabolites from previously economically unfeasible plant sources.

5.1. Production of Transgenic Plants

According to the present invention, a desirable plant or plant cell may be obtained by transforming a plant cell with the nucleic acid encoding an oxygen-binding protein, particularly a globin, and in one embodiment VHb, as described herein. In some instances, it may be desirable to engineer a plant with several different gene constructs. Such engineering may be accomplished by transforming a plant or plant cell with all of the desired gene constructs simultaneously. Alternatively, the engineering may be carried out sequentially. That is, transforming with one gene construct, obtaining the desired transformant after selection and screening, transforming the transformant with a second gene construct, and so on.

In an embodiment of the present invention, Agrobacterium is employed to introduce the gene constructs into plants. Such transformations preferably use binary Agrobacterium T-DNA vectors (Bevan, 1984, *Nuc. Acid Res.* 12: 8711–8721), and the co-cultivation procedure (Horsch et al., 1985, *Science* 227: 1229–1231). Generally, the Agrobacterium transformation system is used to engineer dicotyledonous plants (Bevan et al., 1982, *Ann. Rev. Genet.* 16: 357–384; Rogers et al., 1986, *Methods Enzymol.* 118: 627–641) The Agrobacterium transformation system may also be used to transform, as well as transfer, DNA to monocotyledonous plants and plant cells (see Hernalsteen et al., 1984, *EMBO J.* 3: 3039–3041; Hooykass-Van Slogteren et al., 1984, Nature 311: 763–764; Grimsley et al., 1987, Nature 325: 1677–179; Boulton et al., 1989, Plant Mol. Biol. 12: 31–40.; Gould et al., 1991, Plant Physiol. 95: 426–434).

In other embodiments, various alternative methods for introducing recombinant nucleic acid constructs into plants and plant cells may also be utilized. These other methods are particularly useful where the target is a monocotyledonous plant. Alternative gene transfer and transformation methods include, but are not limited to, protoplast transformation through calcium-, polyethylene glycol (PEG)- or electroporation-mediated uptake of naked DNA (see Paszkowski et al., 1984, EMBO J 3: 2717–2722, Potrykus et al., 1985, Mol. Gen. Genet. 199: 169–177; Fromm et al., 1985, Proc. Natl. Acad. Sci. USA 82: 5824–5828; Shimamoto, 1989, Nature 338: 274–276) and electroporation of plant tissues (D'Halluin et al., 1992, Plant Cell 4: 1495–1505). Additional methods for plant cell transformation include microinjection, silicon carbide mediated DNA uptake (Kaeppler et al., 1990, Plant Cell Reporter 9: 415–418), and microprojectile bombardment (see Klein et al., 1988, Proc. Natl. Acad. Sci. USA 85: 4305–4309; Gordon-Kamm et al., 1990, Plant Cell 2: 603–618).

According to the present invention, a wide variety of plants may be engineered for the desired physiological and agronomic characteristics described herein using nucleic acid constructs encoding oxygen-binding proteins and the various transformation methods mentioned above. Target plants for engineering include, but are not limited to, those of tobacco, Datura, maize, wheat, rice, soybean, tomato, carrots, peanut, potato, sugar beets, sunflower, yam, Arabidopsis, rape seed, and petunia.

According to the present invention, desired plants may be obtained by engineering the gene constructs described herein into a variety of plant cell types, including but not limited to, protoplasts, tissue culture cells, tissue and organ explants, pollen, embryos as well as whole plants. In an embodiment of the present invention, the engineered plant material is selected or screened for transformants (i.e., those that have incorporated or integrated the introduced gene construct(s)) following the approaches and methods described below. An isolated transformant may then be regenerated into a plant. Alternatively, the engineered plant material may be regenerated into a plant, or plantlet, before subjecting the derived plant, or plantlet, to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amounts of the antibiotic or herbicide to which the transforming marker gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods may also be used to identify a plant or plant cell transformant containing the gene constructs of the present invention. These methods include but are not limited to: 1) Southern analysis or PCR amplification for detecting and determining the structure of the recombinant DNA insert; 2) northern blot, S-1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, western blot techniques, immunoprecipitation, or enzyme-linked immunoassays, where the gene construct products are proteins; 5) biochemical measurements of compounds produced as a consequence of the expression of the introduced gene constructs. Additional techniques, such as in situ hybridization, enzyme staining, and immunostaining, may also be used to detect the presence or expression of the recombinant construct in specific plant organs and tissues. The methods for doing all these assays are well known to those skilled in the art.

5.1.1. Plants Transformed to Express Oxygen-binding Proteins

In accordance to the present invention, a plant that expresses a recombinant oxygen-binding protein gene may be engineered by transforming a plant cell with a gene construct comprising a plant promoter operably associated with a sequence encoding oxygen-binding protein. (Operably associated is used herein to mean that transcription controlled by the "associated" promoter would produce a functional messenger RNA, whose translation would produce the enzyme.) The plant promoter may be constitutive or inducible. Useful constitutive promoters include, but are not limited to, the CaMV 35S promoter, the T-DNA mannopine synthetase promoter, and their various derivatives. Useful inducible promoters include but are not limited to the promoters of ribulose bisphosphate carboxylase (RUBISCO) genes, chlorophyll a/b binding protein (CAB) genes, heat shock genes, the defense responsive gene (e.g., phenylalanine ammonia lyase genes), wound induced genes (e.g., hydroxyproline rich cell wall protein genes), chemically-inducible genes (e.g., nitrate reductase genes, gluconase genes, chitinase genes, PR-1 genes etc.), dark-inducible genes (e.g., asparagine synthetase gene (Coruzzi and Tsai, U.S. Pat. No. 5,256,558, Oct. 26, 1993, Gene Encoding Plant Asparagine Synthetase) to name just a few.

In yet another embodiment of the present invention, it may be advantageous to transform a plant with a gene construct operably linking a modified or artificial promoter to a sequence encoding oxygen-binding protein. Typically, such promoters, constructed by recombining structural elements of different promoters, have unique expression patterns and/or levels not found in natural promoters. See, e.g. Salina et al., 1992, Plant Cell 4: 1485–1493, for examples of artificial promoters constructed from combining cis-regulatory elements with a promoter core.

In a preferred embodiment of the present invention, the associated promoter is a strong and/or embryo-specific plant promoter such that the oxygen-binding protein is overexpressed in the transgenic plant. Additionally, particular promoters may be used to direct tissue specific expression of the oxygen-binding protein. For example, root-specific, expression of an oxygen-binding protein may be engineered.

Further, recombinant expression of an oxygen-binding protein may be directed to specific cellular compartments. one of skill in the art may direct expression of the oxygen-binding protein intracellularly, to the chloroplasts, or to the mitochondria, to give just a few examples.

In yet another preferred embodiment of the present invention, the overexpression of oxygen-binding protein in plants may be engineered by increasing the copy number of the oxygen-binding protein gene. One approach to producing such transgenic plants is to transform with nucleic acid constructs that contain multiple copies of a plant expression construct directing the expression of a oxygen-binding protein gene (i.e., operatively linked to a plant promoter). Another approach is to repeatedly transform successive generations of a plant line with one or more copies of the plant expression construct. Yet another approach is to place a oxygen-binding protein expression construct in a nucleic acid construct containing an amplification-selectable marker (ASM) gene such as the glutamine synthetase or dihydrofolate reductase gene. Cells transformed with such constructs are subjected to culturing regimes that select cell lines with increased copies of the oxygen-binding protein gene. See Donn et al., 1984, J. Mol. Appl. Genet. 2: 549–562, for a selection protocol used to isolate of a plant cell line containing amplified copies of the GS gene. Because the desired gene is closely linked to the ASM, cell lines that amplified the ASM gene are also likely to have amplified the desired oxygen-binding protein gene. Cell lines with amplified copies of the oxygen-binding protein gene can then be regenerated into transgenic plants.

5.1.2. Screening of Transformed Plants for those having Desired Altered Traits

It will be recognized by those skilled in the art that in order to obtain transgenic plants having the desired engineered traits, screening of transformed plants (i.e., those having an gene construct of the invention) having those traits may be required. For example, where the plants have been engineered for overexpression of a oxygen-binding protein gene, transformed plants are examined for those expressing the oxygen-binding protein gene at the desired level and in the desired tissues and developmental stages. The plants exhibiting the desired physiological changes, e.g., oxygen-binding protein expression, may then be subsequently screened for those plants that have the desired phenotypic changes at the plant level (e.g., increased chlorophyll, heme, amino acid, or alkaloid biosynthesis, increased fatty acid desaturation, or increased levels of oxmoprotectants such as glycine betaine which requires oxygen for its biosynthesis). The same principle applies to obtaining transgenic plants having tissue-specific expression of a heterologous gene by the use of a tissue specific promoter driven expression construct.

Alternatively, the transformed plants may be directly screened for those exhibiting the desired structural changes. In one embodiment, such screening may be for the color of the transformed plants. In other embodiments, the screening of the transformed plants may be for improved agronomic characteristics (e.g., faster growth, greater vegetative or reproductive yields, or improved protein contents, etc.), as compared to unengineered progenitor plants, when cultivated under various growth conditions (e.g., soils or media containing different amount of nutrients, water content, and/or salt content).

According to the present invention, plants engineered with oxygen-binding protein expression constructs, particularly Vitreoscilla hemoglobin, may exhibit improved vigorous growth characteristics, increased levels of chlorophyll, and of secondary plant metabolites, particularly alkaloids.

Engineered plants and plant lines possessing such improved agronomic characteristics may be identified by examining any of following parameters: 1) the rate of growth, measured in terms of rate of increase in fresh or dry weight, or rate of increase in height; 2) vegetative yield of the mature plant, in terms of fresh or dry weight; 3) the rate of germination; 4) the level of chlorophyll content; 5) the level of a secondary metabolite of interest, such as nicotine, scopolamine, hyoscyamine; and 6) the color of the plant. The procedures and methods for examining these parameters are well known to those skilled in the art.

According to the present invention, a desired plant is one that exhibits improvement over the control plant (i.e., progenitor plant) in one or more of the aforementioned parameters. In an embodiment, a desired plant is one that shows at least 5% increase over the control plant in at least one parameter. In a preferred embodiment, a desired plant is one that shows at least 20% increase over the control plant in at least one parameter. Most preferred is a plant that shows at least 50% increase in at least one parameter.

6. EXAMPLE

Expression of Vitreoscilla Hemoglobin in Tobacco

An extensively investigated plant alkaloid is nicotine, the principal alkaloid found in tobacco (*Nicotiana tabaccum*). The biosynthetic pathways for the tobacco alkaloids have become accepted but regulation of this pathway is not yet fully understood, and all of its enzymes are not characterized (Bush, L. P., 1981, *Recent Adv. Tob. Sci.* 7: 75–106). However, the activity of the final enzyme in nicotine biosynthesis, nicotine synthase, which catalyzes the formation of (s)-nicotine from nicotinic acid and N-methyl-Δ'-pyrrolinium chloride, has proven to be oxygen-dependent (FIG. 1) (Friesen, J. B. and Leete, E., 1990, Tetrahedron Lett. 31: 6295–6298), and the competing pathway from nicotinic acid and N-methyl-Δ'-pyrrolinium chloride to anabasine is not, so far as is known, stimulated by oxygen. Thus, this system was chosen as a first experiment to investigate the effects of increasing oxygen availability by providing oxygen-binding proteins to the plant. In this example, tobacco was transformed with a VHb expression vector via Agrobacterium mediated gene tperformed to detert assays were performed to determine: (i) if the VHb gene was correctly transcribed and translated in tobacco, (ii) the response of nicotine and anabasine accumulation to VHb expression, and, based on other features observed for the VHb-expressing transgenic plants, (iii) chlorophyll content and growth rate of VHb containing plants.

6.1. Experimental protocol

Recombinant DNA techniques and bacterial strains

Plasmid procedures were performed according to the methods described in Sambrook, J. et al., 1990, *Molecular cloning. A laboratory manual*, Cold Spring Harbor, N.Y., Cold Spring Harbor Laboratory Press, and PCR was performed using standard protocols (Saiki, supra). *Escherichia coli* strain TGI (F'traD36lacI9Δ[lacZ]M15proA+B+/supE [hsdM-mcrB]5[$r_K$-$m_K$-McrB-]thi[lac-proAB][lac-pro]) was cultivated and transformed, using standard techniques (Sambrook, J., supra). Restriction enzymes were used according to the suppliers' recommendations (GIBCO BRL, Labdesign). *Agrobacterium tumefaciens* strain LBA 4404 (Walden, R. et al., 1990, *MMCB* 1: 175–194) was cultivated in LB medium (tryptone 10 g/l, yeast extract 5 g/l, NaCl 10 g/l) and transformed with the aid of *E.coli* HB 101, harboring conjugative plasmid pRK 2013 (Figurski, D. H. and Helinski, D. R., 1979, *Proc. Natl. Acad. Sci. U.S.A.* 76: 1648–1652). Extraction of genomic tobacco DNA for PCR analysis was performed as described by Edwards, K. et al., 1991, *Nucleic Acids Res.* 19: 1349).

DNA-constructions

PCR was used to amplify the VHb gene from plasmid pINT1 (Khosla, C. and Bailey J. E., 1989, *J. Mol. Biol.* 210: 79–90). The 5' primer H1 (with sequence 5'-GCA AAC AGG ATC CCG CGT CTA GAG G 3') (SEQ ID NO: 1) was complementary to a region upstream of the transcription initiation codon containing several restriction enzyme sites, the 3' primer H2 (with sequence 5'-GCA GAT TTG TAC GCT CAA GCG GTT GAA TGA GCT CCC AAA G-3') (SEQ ID NO: 2) was complementary to the coding region of the VHb gene upstream of the stop codon; primers were synthesized at the Biomolecular Unit, Lund University. The stop codon was also altered, using PCR mediated mutagenesis, from TAA to TGA, which is a more frequently used stop codon in tobacco. The amplified PCR fragment was inserted into pUC19 which was subsequently transformed into *E. coli*. Bacteria expressing the VHb gene exhibit a red tint when pelleted. One of the best expressing *E. coli* clones, pUH4, was chosen for further experiments. To verify that the cloned PCR fragment of the VHb gene expressed a functional protein, difference spectrum analysis was used (Webster, D. A. and Liu, C. Y., 1974, *J. Biol. Chem.* 249: 4257–4260). Analysis of the CO spectrum of recombinant *E. coli* harboring pUH4 revealed a pronounced peak at 419 nm which is characteristic for the VHb activity (Lilius, supra). The VHb gene fragment was cleaved out with XbaI and SacI and ligated into plasmid pBin121: 2 (Jefferson, R. A., 1987, *Plant. Mol. Biol. Rep.* 5: 387–405) giving pBH4 (FIG. 2).

Plant Material

*Nicotiana tabaccum* SR. plants were exposed to 16 h light at 25° C. and were either kept in soil or in sterile jars on MS-media (Murashige, T. and Skoog, F., 1962, *Physiol. Plant* 15: 473–497). The tobacco plants were transformed by Agrobacterium-mediated gene transfer as described by Rogers, S. G. and Fraley, R. T., 1986, *Methods Enzymol.* 118: 627–684. Stable heterozygous transformants of the $F_1$ generation were used in all plant experiments.

Transcription Analysis using RT-PCR

Polyadenylated mRNA was isolated from 100 mg leaf material using oligo(dT)-cellulose as in the Pharmacia Quick Prep™ manual. The VHb gene transcript was amplified by rTth DNA polymerase and the primers according to the instructions given by Perkin Elmer.

Western Immunoblot Analysis

Protein extracts of two transgenic tobacco lines and a wild-type control were prepared as follows: One gram leaf and stem material was homogenized in 0.1 M sodium phosphate, 5 mM DTT and 5 mM EDTA buffer at pH 7.5. The homogenates were centrifuged in 1.5 mL test tubes at 12,000 rpm for 15 min; the protein-containing supernatants were decanted and used for further studies. The proteins were separated on 15% SDS-PAGE gels and blotted onto Immobilon P nylon membranes supplied by Millipore. The electrophoreses and blotting were performed as described by Laemmli (Laemmli, U. K., 1970, *Nature* 277: 680–685) and Sambrook, supra, respectively. The VHb monomers were detected by VHb antiserum generated in rabbit, and visualized by peroxidase conjugated swine anti-rabbit immunoglobulins (Dako).

Alkaloid Analysis

Transgenic tobacco and wild-type plants were analyzed for their nicotine and anabasine levels. The plants were grown for 30 days on MS medium, then harvested and homogenized in approximately 40 mL 0.1 M Tris-HCl buffer pH 9.0, centrifuged and stored at −70° C. The nicotine and anabasine concentrations were determined using capillary column gas chromatography as described by Curvall et al., 1982, *J. Chrom.* 232: 283–293.

Chlorophyll Assay

Leaf material from three-week old seedlings was homogenized in 1.5 ml tubes and the chlorophyll was extracted with ice-cold 80% acetone. The debris was removed and the supernatants were collected. The absorbance of the chlorophyll extracts were monitored at 645 and 633 nm. The absorbencies were normalized to the amount of plant material used in each extraction. The amounts of chlorophyll-A and B were calculated as described by Arnon, D. I., 1949, *Plant Physiol.* 24: 1–15.

6.2. Results

Preparation of Transgenic Tobacco

A vector was constructed for expression of the VHb gene in plants (FIG. 2). Genomic DNA from several tobacco transformants was purified and analyzed by PCR to determine if the VHb gene was inserted into the genome. Approximately 90% of the analyzed plants were positive. PolyA+ mRNA was isolated from plant leaves of two PCR-positive transgenic plant lines, He3 and He4, and a wild-type control line. Two polynucleotide primers, H1 and H2 (see Experimental protocol), were used in a reverse transcriptase PCR reaction to amplify and detect the mRNA transcript of the VHb gene. Both transgenic tobacco lines exhibited a full-length VHb mRNA transcript which corresponded well to the theoretical size of 460 base pairs.

Expression of VHb protein in tobacco could easily be detected by Western immunoblot analysis on leaf and stem protein extracts. A 15.7 kDa protein that cross-reacted with a VHb antiserum was present in both transgenic tobacco lines but absent in the wild-type control. The level of VHb expression using the 35S CaMV promoter of pBi121: 2 is approximately 0.1% of total protein. However, the presence of several cytochromes in tobacco precluded the use of the CO binding assay for VHb activity (Saiki, et al., 1988, Science 239: 487–491).

Improved Overall Growth in Transgenic Tobacco

Transgenic tobacco seeds of two transgenic lines, He3 and He4, from the F1 generation and a wild-type control were germinated in soil and their development was followed visually and by harvesting plants at regular intervals. Germination was markedly accelerated in plants transformed with VHb-expression constructs, particularly in the transgenic line He4, over that in non-transformed plants. Analysis showed that the germination time for the transformed plants was approximately 3–4 days compared to 6–8 days for wild-type tobacco. Additionally, the growth rates and final yields were higher in the transgenic plants (FIG. 3). For instance, the dried weights were enhanced by 80 to 100% after 35 days of growth. Furthermore, the period between germination and flowering of the transgenic plants was reduced by 3–5 days compared to wild-type.

Alkaloid Analysis of the VHb-expressing Transgenic Tobacco

Extracts of two VHb-expressing transgenic tobacco plant lines, He3 and He4, and a wild-type control were analyzed for nicotine and anabasine content by gas chromatography (FIG. 4). Compared with the wild-type, the transgenic plaints (He3) were holding on average 34% higher ratio of nicotine corresponding to 108 $\mu$g/g dry weight. At the same time, the anabasine levels decreased substantially in the VHb-expressing transgenic plants. The highest yielding individual transgenic tobacco plant had 130 $\mu$g/g dry weight of nicotine which is very similar to the highest nicotine content in tobacco given in the literature (Sheen, S. J., 1988, J. Food Sci. 53: 1572–1573), 140 $\mu$g/g dry weight.

Chlorophyll Content of VHb-expressing Transgenic Tobacco

Visual observation of VHb-expressing tobacco transgenes indicated that many of these plants appeared more green than wild-type control plants. As depicted in FIG. 1B, several steps in chlorophyll and heme biosynthesis are oxygen dependent. Therefore, chlorophyll and growth rate assays were conducted on several F1 generation plants obtained from wild-type tobacco and from the VHb-expressing clones designated He3 and He4. Assays of chlorophyll content showed small but significant increases in chlorophyll content particularly in the He4 plants (FIG. 5). These plants also grew about 20–40% faster than the wild-type as determined by height. Differences in growth rate between transgenic and wild-type plants were not observed when these plants were grown in an atmosphere with reduced oxygen.

6.3. Discussion

Engineering VHb expression in tobacco plants influenced nicotine (and anabasine) production, but indications of more global effects of VHb expression began with the observation that young transgenic plants exhibit a darker green shade of color than do wild-type plants. Subsequent measurements of chlorophyll levels revealed 10–20% increased levels in the He3 plants which also corresponded 20–40% increased growth rates as determined by plant heights. Cloning of VHb in tobacco affected the He3 and He4 plants somewhat differently. Enhanced levels of nicotine and chlorophyll were associated with He3 and He4 plants, respectively. Such differences among clones are common, particularly when using integrating vectors.

One hypothesis to explain this dramatic shift in nicotine and anabasine production in VHb-expressing transgenic tobacco plants, is that the presence of VHb increases the oxygen availability, which in turn significantly affects distribution of secondary metabolite production in the whole tobacco plant. Alternatively, these shifts in secondary metabolite production in VHb-expressing transgenes may result from other metabolic effects of VHb such as an increase in the ATP synthesis rate and/or membrane energy. Availability of more energy in the cell might lead to the improvement of many metabolic functions including increased nicotine production.

7. EXAMPLE

Expression of Vitreoscilla Hemoglobin in Datura

Hyoscyamine and scopolamine are tropane alkaloids produced by plants; hyoscyamine is the levorotatory component of racemic atropine. Atropine, hyoscyamine, and scopolamine affect the parasympathetic nervous system and exhibit a wide range of pharmaceutical activity. In medicine they are used to relieve Parkinson-ism, dilate pupils, increase the heart rate, counteract toxic agents, and reduce secretions such as sweat. Scopolamine produces fewer undesirable side effects than hyoscyamine and is the preferred substance for treatment of motion sickness and production of derivative drugs for gastric disorders. Therefore, there has been a long-standing interest in raising the scopolamine level of producing plants. Datura innoxia a medicinal plant grown in many tropical and sub-tropical countries is one of the principal sources of tropane alkaloids. The biosynthesis of these alkaloids involves several oxygen-requiring steps.

7.1. Experimental Protocol

Recombinant DNA techniques, Transcription analysis and Western immunoblot analysis were performed as above for tobacco. The same transformation vector which was used for tobacco was also used for Datura.

Plant Material

Plants of Datura innoxia Mill were exposed to 16 h light at 24° C. and were kept in sterile jars on basal medium (BM) containing Murashige and Skoog's macro salts, and Nitsch and Nitsch micro salts and vitamins (Sangwan et al., 1991, Plant Cell Rep. 10: 90–93). The plants were transformed by Agrobacterium-mediated gene transfer using the leaf disc method as described by Sangwan et al. (1991). Transformants of the $F_0$ generation were used in this experiment.

Alkaloid Analysis

Transgenic Datura and wild-type plants were analyzed for their scopolamine and hyoscyamine levels. The plants were grown in soil until they were budding, then the leaves were harvested and dried. The scopolamine and hyoscyamine levels were determined using HPLC as described by Gontier et al., 1994, Agro-Food-Ind. Hi-Tech 5, 26–28.

7.2. Results

Several transgenic plants were positive for the VHb gene as determined by PCR of genomic DNA. PolyA$^+$ MRNA was isolated from plant leaves of six PCR-positive transgenic plants and two wild-type plants. All six transgenes exhibited a full-length VHb transcript. Preliminary results showed that the Datura plants transformed with the VHb expression construct also exhibited increased growth rates as compared to the wild-type plants.

Extracts from the six transgenic and two wild-type Datura plants were analyzed for scopolamine and hyoscyamine content by HPLC. Results are presented in the following table.

TABLE I

| Transgenic plant No. | Production of Scopolamine mg/100 g D.W. | Production of Hyoscyamine mg/100 g D.W. |
|---|---|---|
| 1 | 115 | 47 |
| 2 | 148 | 35 |
| 3 | 246 | 20 |
| 4 | 86 | 28 |
| 5 | 118 | 17 |
| 6 | 70 | 10 |
| Control A | 26 | 7.1 |
| Control B | 55 | 8.0 |

7.3. Discussion

Similarly to the results in tobacco, engineering Datura plants to express a VHb gene also resulted in transformed plants which both grew faster and contained altered levels of desired secondary metabolites. These results show that the expression of oxygen-binding proteins in whole plants, particularly proteins which reversibly bind oxygen via a heme group such as VHb, is generally applicable to obtain improved transformed plants.

8. EXAMPLE

Phenotypic Screen for Vitreoscilla Hemoglobin Mutants

In order to create a library of randomly mutated VHbs, we used an earlier construct, pINT1 which carries the VHb gene as a template (Khosla and Bailey, 1989, supra.). The VHb sequence used as a template encoded the wild-type VHb protein with an additional 8 amino acid extension—MTMITPSF (SEQ ID NO: 3)—at the amino-terminal end of the protein. However, all numbering conventions given herein correspond to the wild-type amino acid sequence positions as described in U.S. Pat. No. 5,049,493 supra.. The VHb gene was amplified by low fidelity PCR with an estimated error rate of 2–4% (Leung et al., 1989, Technique, 1, 11–15) using primers H1 and H2.

8.1. Experimental Protocol

PCR

Low fidelity PCR was performed with 1 mM dCTP, dGTP and dTTP, 0.2 mM dATP, 0.45 mM of each primer, 0.1 ng template, 1% 1 M mercaptoethanol, 10% DMSO, 0.5 mM MnCl$_2$ and 10 U Taq DNA polymerase. A temperature profile was employed of 2 min. at 95° C., hold at 70° C. while the Taq DNA polymerase was added, 30 cycles of 15 sec. at 92° C., 30 sec. at 50° C., 1 min. at 72° C. and an additional 5 cycles of 15 sec. at 92° C., 5 min. at 72° C. The amplified PCR fragments were inserted into pUC19 which was subsequently transformed into E coli. Sequencing of the mutated genes was performed on an automatic sequencer with the terminator chemistry.

Screening the Library for Colonies Carrying Mutated VHb

The plasmid library was transformed into E. coli. TG1 and selected on LB agar (Sambrook et al.) by visually assessing the color of the colonies. Expression of wild-type VHb results in a red colored colony. The red color phenotype is indicative of a VHb protein capable of binding oxygenated heme. Approximately 10,000 colonies were identified ranging in color from white to deep red.

Western Immunoblot Analysis

Overnight cultures were pelleted, resuspended in a sodium phosphate buffer (50 mM, pH 7.0) and sonicated to obtain protein extracts. The proteins were separated on 15% SDS-PAGE gels and blotted onto Immobilon P nylon membranes supplied by Millipore. The electrophoresis and blotting were performed as described by Laemmli (1970) and Sambrook et al. (1989), respectively. The VHb mutants were detected by VHb antiserum generated in rabbit, and visualized by peroxidase conjugated swine anti-rabbit immunoglobulins (Dako).

8.2. Results

Randomly picked colonies, which exhibited the correct size VHb (15.7 kDa) according to Western blot, were sequenced. The following altered VHb amino acid sequences were identified.

TABLE II

| ALTERED VHB PROTEINS OBTAINED THROUGH PCR MUTAGENESIS | |
|---|---|
| ISOLATE | AMINO ACID ALTERNATION |
| A | Ile$^{129}$Thr |
| B | His$^{36}$Arg |
| C | Lys$^{79}$Asn |
| D | Phe$^{33}$Tyr, Gln$^{53}$Arg |
| E | Lys$^{124}$Glu, Phe$^{133}$Leu, Ile$^{134}$Thr |
| F | Gly$^{21}$Asp, Val$^{136}$Glu, Ala$^{138}$Thr |
| G | Leu$^{51}$Ser, Val$^{83}$Ala, Tyr$^{126}$His |
| H | Lys$^{11}$Glu, Lys$^{107}$Glu, Lys$^{124}$Stop |

8.3. Discussion

The PCR mutagenesis technique allowed the phenotypic selection of VHb mutants which retain at least some functional activity of the VHb, as evidenced by their ability to bind oxygenated heme. Although these mutants were generated in a VHb protein with an 8 amino acid amino-terminal extension, these mutants will be similarly effective in a VHb protein with the wild-type amino-terminus. Further, this approach will enable the easy selection and generation of any altered hemoglobin molecule through mutagenesis of the coding sequence, followed by selection for clones which encode heme containing proteins which retain functional activity.

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings such modifications are intended to fall within the scope of the appended claims various publications are cited herein, each of the disclosures of which is incorporated by reference in its entirety.

What is claimed is:

1. A plant which has been genetically engineered by transformation with a polynucleotide encoding a Vitreoscilla hemoglobin or a polynucleotide that hybridizes under highly stringent conditions to the complement of the polynucleotide that encodes the Vitreoscilla hemoglobin and encodes an oxygen-binding protein.

2. The plant of claim 1, wherein the polynucleotide encoding the Vitreoscilla hemoglobin, or the polynucleotide that hybridizes under highly stringent conditions to the complement of the polynucleotide that encodes the Vitreoscilla hemoglobin, is operably linked to a plant promoter.

3. The plant of claim 2, wherein the plant promoter is a strong, constitutively expressed plant promoter.

4. The plant of claim 3, wherein said strong, constitutively expressed plant promoter is a CaMV 35S promoter.

5. The plant of claim 2, wherein the plant promoter is a tissue specific plant promoter.

6. The plant of claim 1, wherein the polynucleotide is transformed into the plant on a Ti plasmid.

7. The plant of claim 1, wherein the polynucleotide is transformed into the plant via microprojectile bombardment.

8. The plant of claim 1, wherein the plant is a dicotyledons.

9. The plant of claim 1, wherein the plant is a monocotyledons.

10. The plant of claim 1, wherein the plant is selected from the group consisting of tobacco, Datura, maize, wheat, rice, soybean, tomato, carrots, peanut, potato, sugar beets, sunflower, yam, Arabidopsis, rape seed, and petunia.

11. The plant of claim 8, wherein the plant is from the genus Nicotiana.

12. The plant of claim 11, wherein the plant is *Nicotiana tabacum*.

13. The plant of claim 8, wherein the plant is from the genus Datura.

14. The plant of claim 1, wherein the Vitreoscilla hemoglobin is selected from the group consisting of $Vhb^{ile129thr}$, $Vhb^{his36arg}$, $Vhb^{lys79asp}$, $Vhb^{phe33tyr, gln53arg}$, $Vhb^{lys124glu, phe133leu, ile134thre}$, $Vhb^{gly21asp, val136glu, ala138thr}$, $Vhb^{leu51ser, val83ala, tyr126his}$ and $Vhb^{lys11glu, lys107glu, lys124stop}$.

15. The method of claim 14, wherein the Vitreoscilla hemoglobin is selected from the group consisting of $Vhb^{ile129thr}$, $Vhb^{his36arg}$, $Vhb^{lys79asp}$, $Vhb^{phe33tyr, gln53arg}$ Vhb$^{lys124glu, phe133leu, ile134thre}$, Vhb$^{gly21asp, val136glu, ala138thr}$, Vhb$^{leu51ser, val83ala, tyr126his}$ and Vhb$^{lys11glu, lys107glu, lys124st

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:1:

GCAAACAGGA TCCCGCGTCT AGAGG  25

(2) INFORMATION FOR SEQ ID NO:2:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:2:

GCAGATTTGT ACGCTCAAGC GGTTGAATGA GCTCCCAAAG  40

(2) INFORMATION FOR SEQ ID NO:3:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:3:

Met Thr Met Ile Thr Pro Ser Phe
1               5